United States Patent

Sheard et al.

[11] 4,094,926
[45] June 13, 1978

[54] POLYMERIC PHOSPHORUS COMPOUNDS AND FLAME RETARDANT POLYETHYLENETEREPHTHALATE CONTAINING SAID POLYMERS

[75] Inventors: Dennis Richard Sheard; Ian Stuart Fisher, both of Harrogate, England

[73] Assignee: Imperial Chemical Industries Limited, London, England

[21] Appl. No.: 659,628

[22] Filed: Feb. 20, 1976

[30] Foreign Application Priority Data

Mar. 11, 1975 United Kingdom ............... 10057/75

[51] Int. Cl.² ...................... C08G 65/40; C08L 67/02
[52] U.S. Cl. .................. 260/860; 260/45.7 P; 260/47 P; 260/75 P; 260/896; 260/929; 260/DIG. 24; 260/930; 526/2; 526/27
[58] Field of Search ............ 260/47 P, 929, DIG. 24, 260/860, 45.7 P, 75 P, 930

[56] References Cited

U.S. PATENT DOCUMENTS

| | | | |
|---|---|---|---|
| 2,716,101 | 8/1955 | Coover, Jr. et al. ................. | 260/61 |
| 2,891,915 | 6/1959 | McCormack et al. ................. | 260/2 |
| 3,378,524 | 4/1968 | Larrison .................. | 260/47 |
| 3,491,061 | 1/1970 | Millich et al. .......................... | 260/47 |
| 3,641,219 | 2/1972 | Stockburger ........................ | 260/929 |
| 3,655,586 | 4/1972 | Vanderburg .......................... | 260/2 P |

*Primary Examiner*—Lester L. Lee
*Attorney, Agent, or Firm*—Cushman, Darby & Cushman

[57] ABSTRACT

Phosphorus-containing compounds of the formula

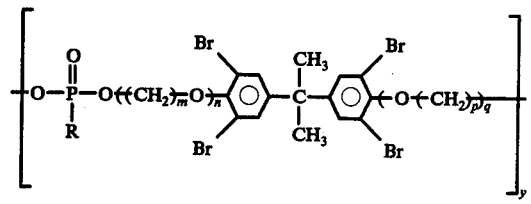

wherein R is phenyl or alkyl of 1 to 4 carbon atoms, $m$ and $p$ are each integers from 2 to 6, $n$ and $q$ are each integers from 1 to 10, $y$ is an integer of at least 2, and flame retardant polymers containing such phosphorus-containing compounds.

12 Claims, No Drawings

POLYMERIC PHOSPHORUS COMPOUNDS AND FLAME RETARDANT POLYETHYLENETEREPHTHALATE CONTAINING SAID POLYMERS

The present invention relates to polymeric phosphorus-containing compounds and their use as flame-retardants for fibre- and film-forming polymers.

According to the present invention we provide a phosphorus-containing compound of the formula

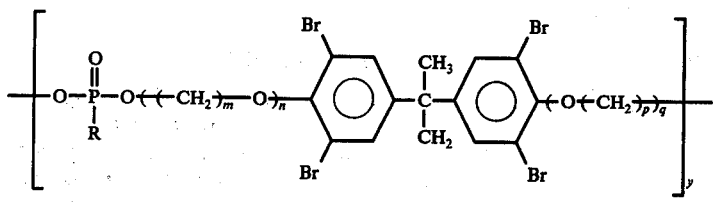

(I)

wherein R is phenyl or alkyl of 1 to 4 carbon atoms.
 $m$ and $p$ are each independently integers from 2 to 6,
 $n$ and $q$ are independently integers from 1 to 10,
 $y$ is an integer of at least 2.

We prefer that $y$ should be at least 3. We prefer that $y$ should not exceed 30.

we prefer that $m$ and $p$ are each 2.

We prefer that $n$ and $q$ are each 1.

The polymeric phosphorus compounds according to the present invention may be prepared by the reaction of a phosphorus compound of the formula:

wherein R is phenyl or alkyl of 1 to 4 carbon atoms, with a compound of the formula:

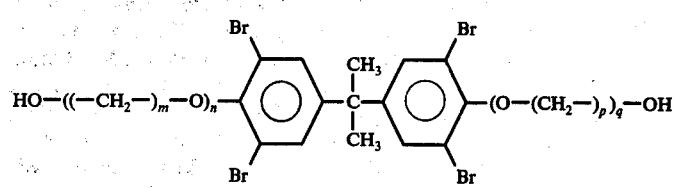

wherein $m$, $n$, $p$ and $q$ have the same significance as indicated hereinbefore, under conditions for the removal of hydrogen chloride.

The end groups of the polymeric phosphorus-containing molecule are those resulting from the method of manufacture.

We particularly prefer the compound:

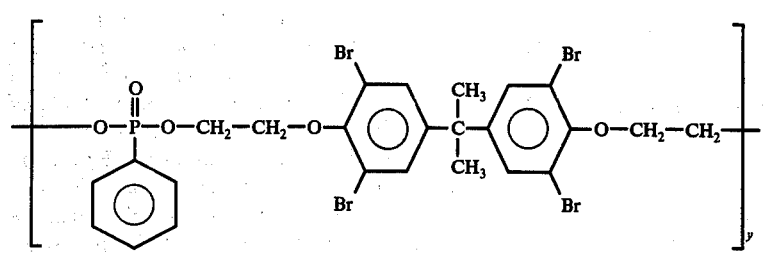

(III)

which may be obtained by the reaction of the phosphorus compound

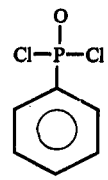

with tetrabromobisphenol A ethoxylate:

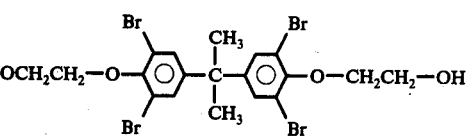

According to the present invention we also provide a flame retardant polymer comprising a minor proportion of a phosphorus-containing compound of the formula:

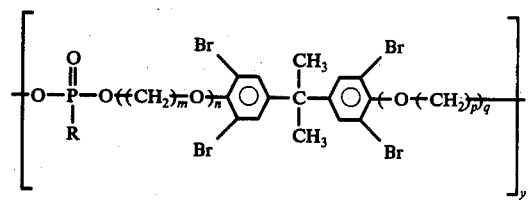

(II)

wherein the significance of $m$, $n$, $p$ and $q$ is the same as indicated hereinbefore.

Preferably the flame-retardant additive should mainly remain unreacted with the polymer with which it is mixed. In the case of polyester a small proportion of the additive will usually react, but this is acceptable.

Preferably the proportion of the flame-retardant phosphorus-containing compound should be from 0.5% to 25% by weight based on the sum of polymer and flame-retardant phosphorus-containing compound.

Polymers in which the flame-retardant phosphorus-containing compounds according to the present invention may be incorporated include polyesters and polyolefines.

The polymers comprising the flame-retardant phosphorus-containing compounds according to the present invention may be formed into fibres, filaments, films or mouldings.

Other additives commonly present in such polymers may be present in addition to the phosphorus-containing compounds according to the present invention in the proportion commonly employed, for example delustrants, colouring materials, antistatic additives, optical whiteners. There may also be present a proportion of an antimony compound to improve the flame-retardant effect.

In the following examples of the present invention, parts are by weight. The Limiting Oxygen Index was determined as follows:

The inherent resistance to flammability of the samples was measured by the Limiting Oxygen Index technique (LOI). This is described in ASTM-D2863 - 70. The sample is fixed vertically in a U-shaped holder to give an exposed area 150 mm high × 38 mm wide and placed in a vertical glass chimney of diameter 95 mm and height 310 mm. A mixture of oxygen and nitrogen is passed up the chimney at a flow speed of 4 cm/sec. The upper edge of the sample is contracted with a butane gas flame while the oxygen concentration is varied. The LOI value is the lowest oxygen concentration (expressed as a volume percent of the total oxygen/nitrogen mixture) at which the sample burns for 3 minutes or 50 mm down the sample. In order to prevent dripping/shrinkage behaviour from interfering with the test, three vertical rows of glass yarn are sewn into the sample (one running up the centre of the sample, the other two running parallel and spaced 12 mm either side of the centre yarn). These glass fibre yarns act as a wick.

The higher the LOI value, the greater is the inherent resistance of the sample to flammability. LOI values of 25 or greater for polyester can be regarded as imparting a very substantial level of resistance to flammability.

EXAMPLE 1

2,2-bis[4-(2-hydroxyethoxy)-3,5-dibromophenyl]propane (60.7 parts) and phenyl phosphonic dichloride (19.5 parts) with anhydrous calcium chloride (0.10 parts) were heated with stirring under nitrogen slowly to 200° C. over about 6 hours. The pressure was then reduced to 100 mm Hg whilst the temperature was raised to 240° – 250° C. over 30 minutes and maintained thus for 10 minutes. After cooling under nitrogen the product was a brittle, light brown, transparent solid. Melting point ca. 90° C. The viscosity ratio (being the ratio of flow times of a 2% solution (weight to volume of solvent) in chloroform to that of the solvent along in an Ostwald viscometer at 25° C.) was 1.08. The molecular weight of the product was that corresponding to Formula III in which $y$ is 2.

EXAMPLE 2

2,2-bis[4-(2-hydroxyethoxy)-3,5-dibromophenyl]propane (124.9 parts) and phenyl phosphonic dichloride (39.0 parts) with anhydrous calcium chloride (0.14 parts) were dissolved in 1,1,2,2-tetrachloroethane under nitrogen with stirring. The mixture was heated in an oil bath slowly over 8 hours to a bath temperature of 200° C. and held at that temperature under strong reflux for 6 hours. After allowing to cool, a further 108 cc of tetrachloroethane was added and the resultant solution added in a slow stream to 1800 cc of vigorously agitated methanol. A viscous oil separated to the bottom. Supernatant liquor was decanted off and the residue heated in vacuo at 90° C. to remove solvent. On cooling the product was a pale brown transparent solid, melting point 70° – 90° C. Viscosity ratio (2% in chloroform) was 1.09.

EXAMPLE 3

Oligomer as prepared in Example 2 (50 parts) was dissolved in 200 cc chloroform, 300 cc methanol was added, the mixture shaken and allowed to separate overnight. The viscous bottom layer was run off and the solvent evaporated under reduced pressure at 100° C. On cooling, the residue set to a brittle solid (16.8 parts).

Viscosity ratio (2% in chloroform) was 1.11.

EXAMPLE 4

135 parts polyethylene terephthalate polymer chip (intrinsic viscosity 0.67), prepared by the use of antimony trioxide as catalyst, was mixed with 15 parts of powdered oligomer from Example 1 and dried by heating at 130° C. at a pressure of 100 mm Hg for 5 hours.

The dried mixture was melted at 275° C. under a stream of nitrogen and stirred for 10 minutes. The molten polymer was then extruded in a thin stream and quenched in a cold water bath. The polymer lace was broken up, re-dried in vacuo, and 100 g compressed into a cylindrical rod by heating in a mould at 220° C. under pressure of 5.25 kg cm$^{-2}$. The resultant rod of polymer was transferred to the barrel of a rod-spinning machine operating at a melt temperature of 262° C. and spun under hydraulic pressure of 4 kg cm$^{-2}$ through a six hole spinneret at a rate of 3 gm/min. Three five-minute doffs were collected at a wind-up speed of 1000 ft/min. These were plied together and drawn 3.5:1 over a hot pin (at 80° C.) and plate (at 100° C.) to give a 76 decitex yarn which was knitted into stockinette on a circular knitting machine. This stockinette when tested according to the method described above had a Limiting Oxygen Index of 29.1. A comparable sample of stockinette made from unblended polyethylene terephthalate polymer had a Limiting Oxygen Index of 22.0.

EXAMPLE 5

The procedure of Example 4 was repeated using respectively samples of the phenyl phosphonate oligomer obtained as described in Examples 2 and 3. No trouble was experienced during spinning of the blends but the yarn from the blend with the oligomer from Example 2 showed a tendency to break during drawing and knitting. For comparative purposes a draw ratio of 3.0:1 was employed. The results of measurements of Limiting Oxygen Index and viscosity ratio of the yarns are shown in the Table. Viscosity ratio (or VR) is measured as the ratio of flow times in an Ostwald viscometer of a 1% (weight to volume of solvent) solution of the polymer in o-chlorophenol compared with the solvent above.

| Sample | Polymer VR | Yarn VR | Limiting Oxygen Index |
|---|---|---|---|
| Oligomer from Example 2 | 1.47 | 1.46 | 25.8 |
| Oligomer from Example 3 | 1.50 | 1.47 | 25.9 |
| Control with no oligomer | 1.70 | 1.68 | 20.4 |

What we claim is:

1. A phosphorus-containing compound of the formula:

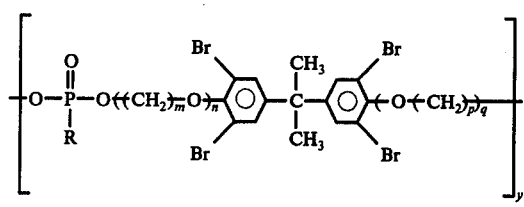

wherein R is phenyl or alkyl of 1 to 4 carbon atoms.
$m$ and $p$ are each independently integers from 2 to 6,
$n$ and $q$ are each independently integers from 1 to 10,
$y$ is an integer of at least 2.

2. A phosphorus-containing compound according to claim 1 wherein $y$ is no less than 3.

3. A phosphorus-containing compound according to claim 1 wherein $y$ does not exceed 30.

4. A phosphorus-containing compound according to claim 1 wherein $m$ and $p$ are each 2.

5. A phosphorus-containing compound according to claim 1 wherein $n$ and $q$ are each 1.

6. A compound of the formula:

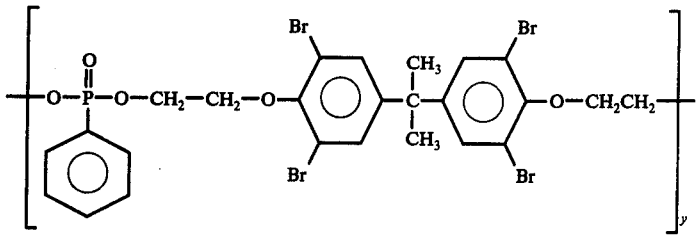

wherein $y$ is an integer of at least 2.

7. Flame retardant polyethylene terephthalate comprising a minor proportion of a compound according to claim 1.

8. A shaped article produced from the flame retardant polyethylene terephthalate of claim 7.

9. Flame retardant polyethylene terephthalate comprising from 0.5% to 25% by weight of a compound according to claim 1, based on the sum of the weights of the polyethylene terephthalate and the compound.

10. Flame retardant polyethylene terephthalate comprising a minor proportion of a compound according to claim 6.

11. A shaped article produced from the flame retardant polyethylene terephthalate of claim 10.

12. Flame retardant polyethylene terephthalate comprising from 0.5% to 25% by weight of a compound according to claim 6, based on the sum of the weights of the polyethylene terephthalate and the compound.

* * * * *